(12) United States Patent
Giambattista et al.

(10) Patent No.: US 6,932,794 B2
(45) Date of Patent: Aug. 23, 2005

(54) MEDICATION DELIVERY PEN

(75) Inventors: Lucio Giambattista, East Hanover, NJ (US); Antonio Bendek, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 236 days.

(21) Appl. No.: 10/406,302

(22) Filed: Apr. 3, 2003

(65) Prior Publication Data

US 2004/0199117 A1 Oct. 7, 2004

(51) Int. Cl.⁷ .................................................. A61M 5/00
(52) U.S. Cl. ........................ 604/207; 604/208; 604/211
(58) Field of Search ................................. 604/207, 208, 604/211, 209, 210, 232, 218, 224

(56) References Cited

U.S. PATENT DOCUMENTS

| | | |
|---|---|---|
| 4,936,833 A | 6/1990 | Sams |
| 5,304,152 A | 4/1994 | Sams |
| 5,308,340 A | 5/1994 | Harris |
| 5,383,865 A | 1/1995 | Michel |
| 5,514,097 A | 5/1996 | Knauer |
| 5,584,815 A | 12/1996 | Pawelka et al. |
| 6,248,095 B1 | 6/2001 | Giambattista et al. |

*Primary Examiner*—Sharon Kennedy
(74) *Attorney, Agent, or Firm*—David M. Fortunato

(57) ABSTRACT

A medication delivery pen is provided including a leadscrew having a plurality of threads; a driver coaxially disposed about at least a portion of the leadscrew; a dosing ring non-rotatably disposed on the driver, the dosing ring also being slidable along the driver; and, a dose knob coaxially disposed about the dosing ring. At least one tooth is formed on one of the dose knob and the dosing ring, and at least one groove is formed on the other of the dose knob and the dosing ring, with the groove being formed to receive the tooth. The dosing ring is selectively movable relative to the dose knob from a first position where the tooth and the groove are spaced apart to a second position where the tooth is received within the groove, the dosing ring being rotatable with the dose knob with the dosing ring being in the second position. Incorrect dosage settings of the inventive pen may be easily corrected by a user via a novel dial-back feature that enables the user to reset the dose amount without expelling medication and without having to dial the dose knob to an extended, reset position.

18 Claims, 9 Drawing Sheets

MEDICATION DELIVERY PEN

BACKGROUND OF THE INVENTION

This invention relates to medication delivery instruments and, more particularly, to medication delivery pens, such as those used in administering insulin.

Various medication delivery pen designs are known in the prior art, including that shown in U.S. Pat. No. 6,248,095, which issued on Jun. 19, 2001, to one of the inventors herein and the assignee hereto. To administer a dose of medication, such as insulin, using the pen of U.S. Pat. No. 6,248,095, and as is commonly done with other medication delivery pen designs, a dose knob is manually rotated until a desired dose amount is set. Thereafter, a needle cannula is inserted into a patient and a button located at the end of the dose knob is depressed resulting in the administration of the desired dose. U.S. Pat. No. 6,248,095 is incorporated herein by reference in its entirety.

Prior art medication delivery pens, however, suffer from the drawback that if the dose knob is adjusted beyond a desired dose (i.e., an error in dosing is made), a waste of time or medication results in correcting to the desired amount. In one manner of correcting for the mistake, the dose knob can be "dialed back" to the lower dose amount and there set. However, such "dialing back" will result in the wasteful expulsion of medicine commensurate to the amount corrected. For example, if the pen is "dialed back" from a 300 µl dosage to a 250 µl dosage, 50 µl will be wastefully expelled. Alternatively, some pens, such as that disclosed in U.S. Pat. No. 6,248,095, provide for a reset mechanism which allows for the dose knob to be disengaged and returned to a zero position without "dialing back". Such reset typically involves "dialing out" the dose knob to its fullest extent where it is disengaged and then returning the dose knob back to a start position. Although it is possible to reset the pen, additional time and effort is required to do so.

SUMMARY OF THE INVENTION

The present invention provides a medication delivery pen which overcomes the deficiencies of the prior art. The medication delivery pen includes a leadscrew having a plurality of threads; a driver coaxially disposed about at least a portion of the leadscrew; a dosing ring non-rotatably disposed on the driver, the dosing ring also being slidable along the driver; and, a dose knob coaxially disposed about the dosing ring. At least one tooth is formed on one of the dose knob and the dosing ring, and at least one groove is formed on the other of the dose knob and the dosing ring, with the groove being formed to receive the tooth. The dosing ring is selectively movable relative to the dose knob from a first position where the tooth and the groove are spaced apart to a second position where the tooth is received within the groove, the dosing ring and the dose knob being rotatable with the dosing ring in the second position.

With the subject invention, the dose knob can be dialed freely in both directions, without causing medicine to be administered, particularly upon "dialing back". In addition, resetting of the dose knob is altogether avoided in allowing for a downward-correction in dosage amount.

These and other features of the subject invention will be better understood through a study of the following detailed description and accompanying drawings.

DETAILED DESCRIPTION OF THE INVENTION

Figure 1:
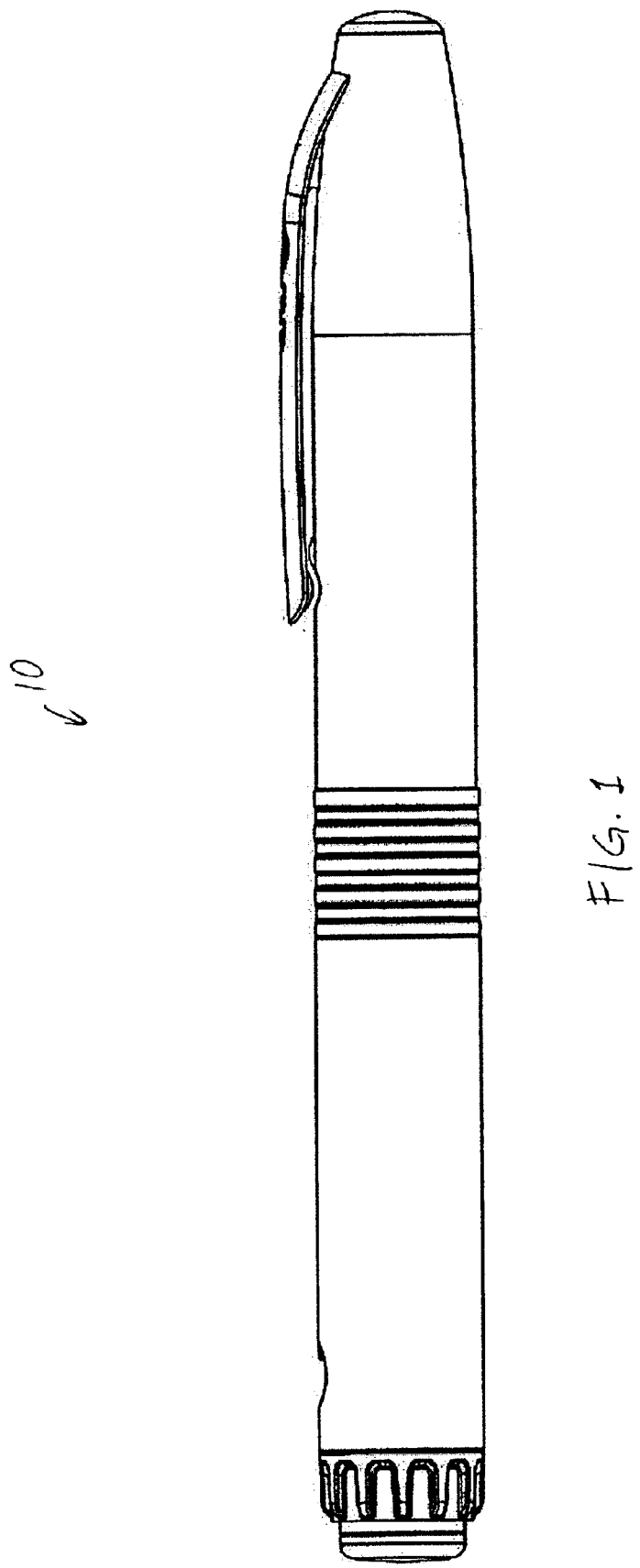
FIG. 1 is a side-elevational view of a medication delivery pen constructed in accordance with the subject invention.

With reference to the Figures, particularly FIG. 1, a medication delivery pen is shown and generally designated with the reference numeral 10. The medication delivery pen 10 may be used for the administration of various medications, including insulin; the medication not comprising a part of the present invention. In addition, the term "medication" is used in an illustrative and non-limiting manner to refer to any substance that may be injected into a patient for any purpose. The medication delivery pen 10 of the present invention may also be reusable or disposable.

Figure 2:
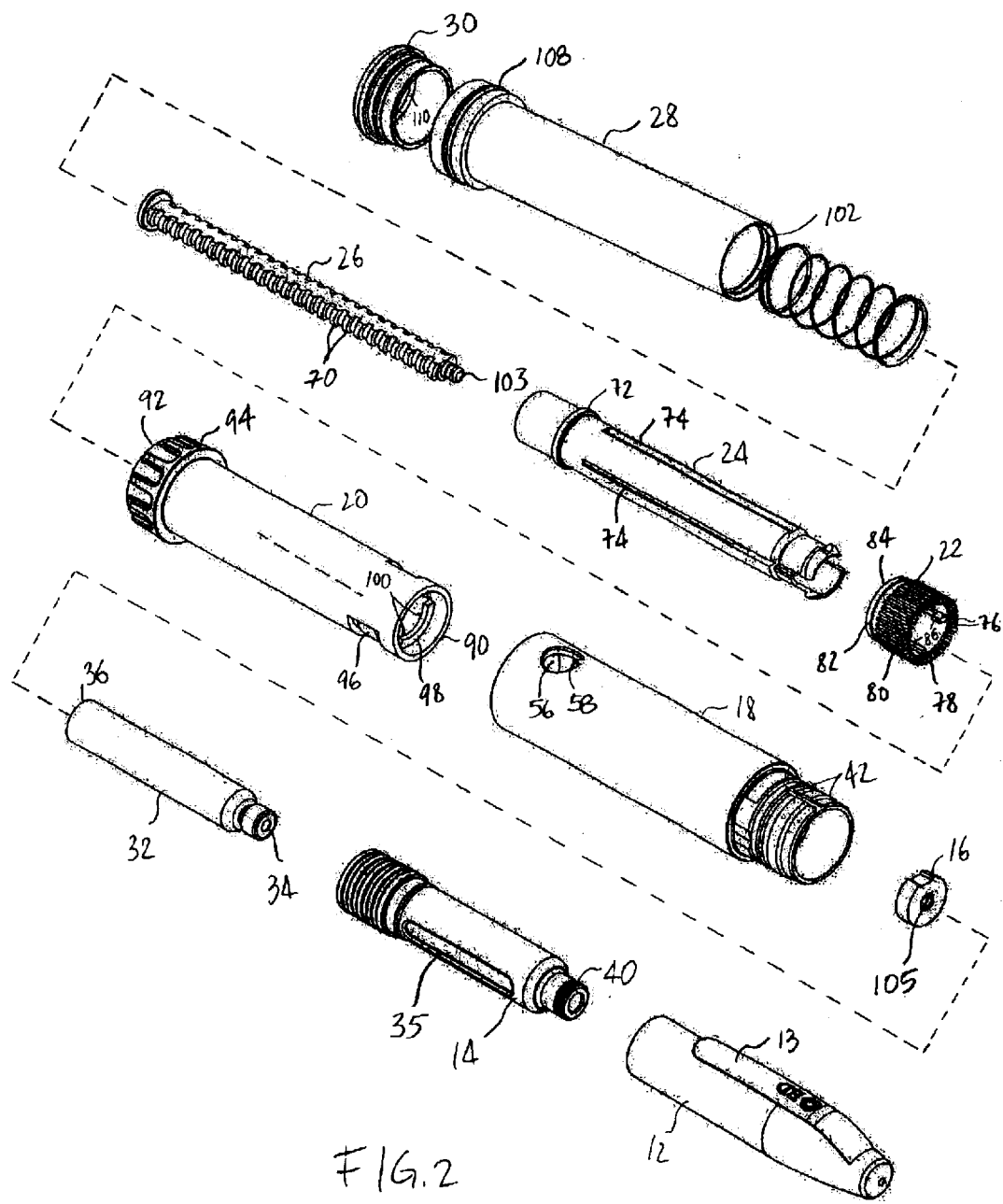
FIG. 2 is an exploded view of a medication delivery pen constructed in accordance with the subject invention.
Figure 7:
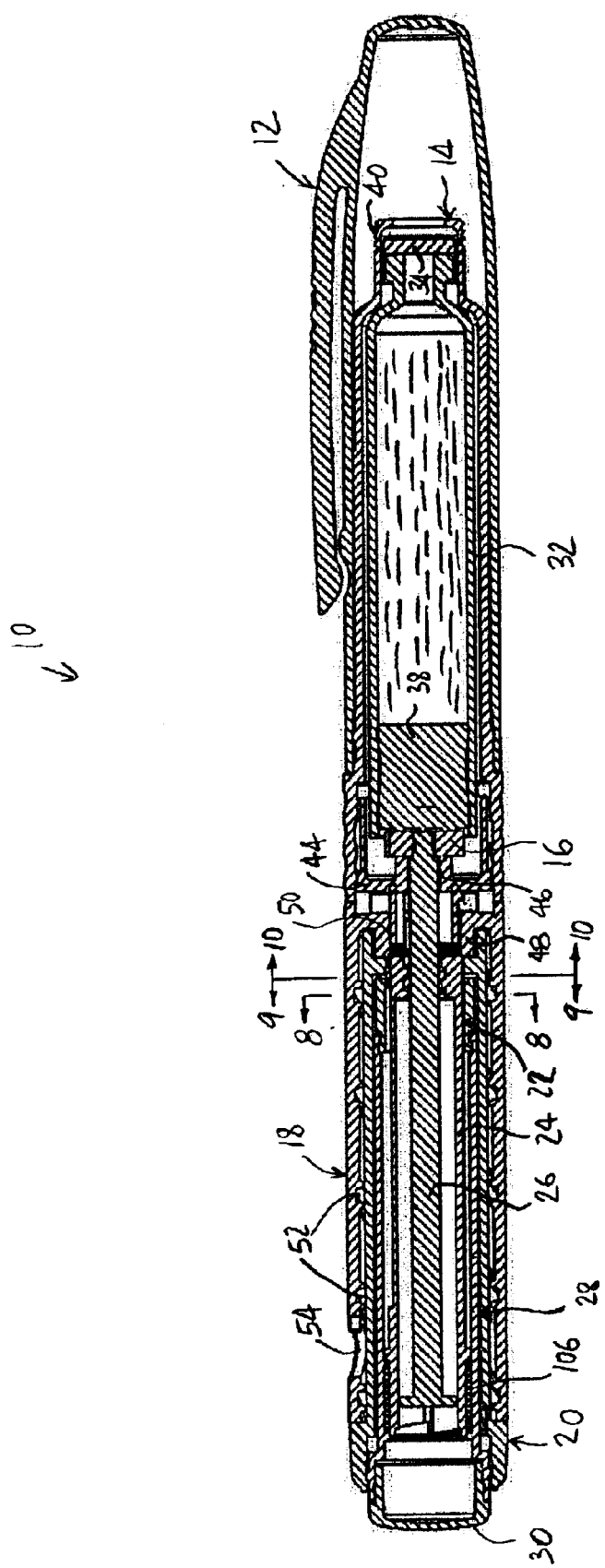
FIG. 7 is a cross-section of a medication delivery pen constructed in accordance with the subject invention.

With reference to FIG. 2, the medication delivery pen 10 generally includes a cap 12, a cartridge holder 14, a spinner 16, a body 18, a dose knob 20, a dosing ring 22, a driver 24, a leadscrew 26, a dosing ring adaptor 28, and a thumb button 30. The cartridge holder 14 is formed to accommodate a drug cartridge 32, which may be of any conventional design. By way of non-limiting example, the drug cartridge 32 may include an elastomeric septum 34 at a proximal end thereof and an open distal end 36 which exposes a slidable plunger 38 (FIG. 7). Drug medication is contained within the drug cartridge 32 between the septum 34 and the plunger 38. As will be described in more detail below, the spinner 16 is configured to engage the plunger 38 and force forward movement thereof in expelling drug from the drug cartridge 32. A needle (not shown) is required to administer drug from the medication delivery pen 10. The needle may be a double-ended cannula which is threadedly mounted onto threads 40 of the cartridge holder 14. One end of the cannula is exposed for insertion into a patient, while the second end of the cannula is disposed to pierce the septum 34 of the drug cartridge 32. After administration of the dose, the needle is removed, with the septum 34 self-sealing. The cap 12 is formed to releasably mount onto the cartridge holder 14, such as with a snap fit, to limit contamination of the septum 34 and the surrounding portions of the cartridge holder 14. A resilient holding arm 13 may extend from the cap 12 to provide holding force for the pen 10 in a patient's pocket. One or more windows 35 may also be provided in the cartridge holder 14 to give a visual indication of the drug level in the drug cartridge 32.

Figure 3:
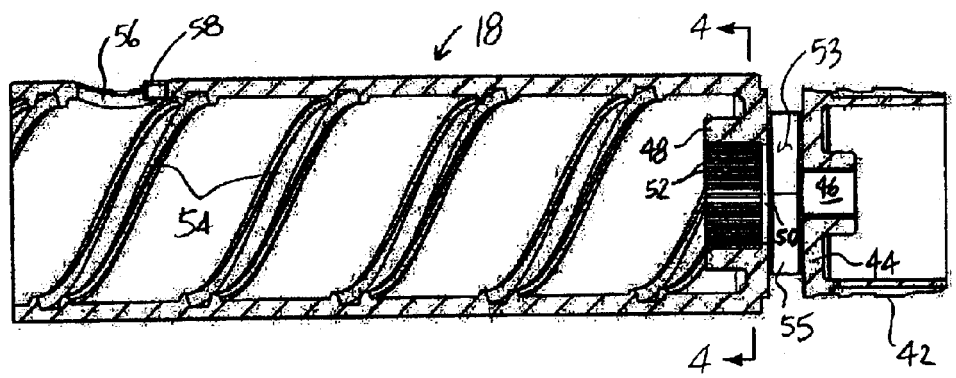
FIG. 3 is a cross-sectional view of a body useable with the subject invention.

With reference to FIG. 3, the body 18 is generally cylindrical, having threads or detents 42 onto which the cartridge holder 14 is formed to be mounted. A bulkhead 44 extends across the interior of the body 18 through which an aperture 46 is formed. The aperture 46 is defined to allow the passage therethrough of the leadscrew 26, yet the aperture 46 is shaped (e.g., being rectangular) to prevent rotation of the leadscrew 26 therewithin. The body 18 also includes an interiorly-supported cylindrical wall 48 which defines a channel 50 therethrough. A transverse recess 53 is defined between the aperture 46 and the channel 50 which is bounded by wall 55, that may be continuous or discontinuous. In addition, a dose setting thread 54, as known in the prior art, is formed on the interior of the body 18, along with a window 56 for dosage selection. A pointer 58 defined on the body 18 may extend into the window 56 to clearly point out a selected dosage level.

Figure 5:
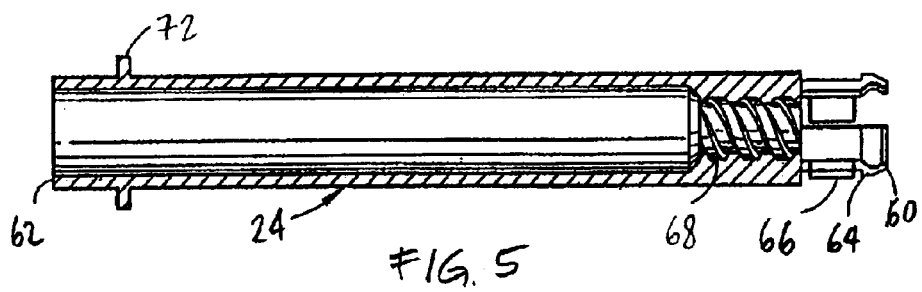
FIG. 5 is a cross-sectional view of a driver useable with the subject invention.

With reference to FIG. 5, the driver 24 includes proximal and distal ends 60 and 62, respectively, with a snap ring 64 being formed at the proximal end 60. The snap ring 64 is formed to pass through the channel 50 of the body 18 and lock onto the wall 48 in the recess 53 (FIG. 7). With the snap ring connection, the driver 24 is fixed axially relative to the body 18, yet is able to rotate relative thereto. Internal threads 68 are also provided to threadedly engage threads 70 of the leadscrew 26. Additionally, as shown in FIG. 2, ledge 72 and one or more longitudinal keyways 74 are defined on the exterior surface of the driver 24.

Figure 4:
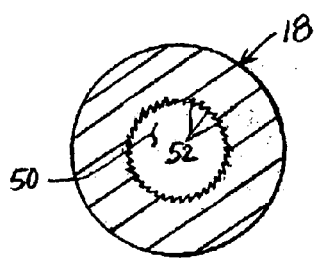
FIG. 4 is a cross-sectional view taken along line 4—4 of FIG. 3.
Figure 6:
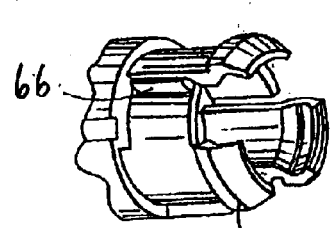
FIG. 6 is an enlarged perspective view of a proximal end of the driver shown in FIG. 5.

Preferably, as more clearly shown in FIG. 4, a plurality of ratchet teeth 52 extend from the cylindrical wall 48. In addition, one or more ratchet fingers 66 are formed on the proximal end 60 of the driver 24 and are located in proximity to the snap ring 64. The ratchet fingers 66 are positioned within the channel 50 when the driver 24 is locked in the recess 53 (FIG. 7). Preferably, the ratchet teeth 52 and the ratchet fingers 66 cooperate to allow the driver 24 to rotate in only one direction relative to the body 18. The ratchet teeth 52 and the ratchet fingers 66 provide a measure of protection against unwanted rearward movement of the leadscrew 26, as described more fully below.

Figure 9:
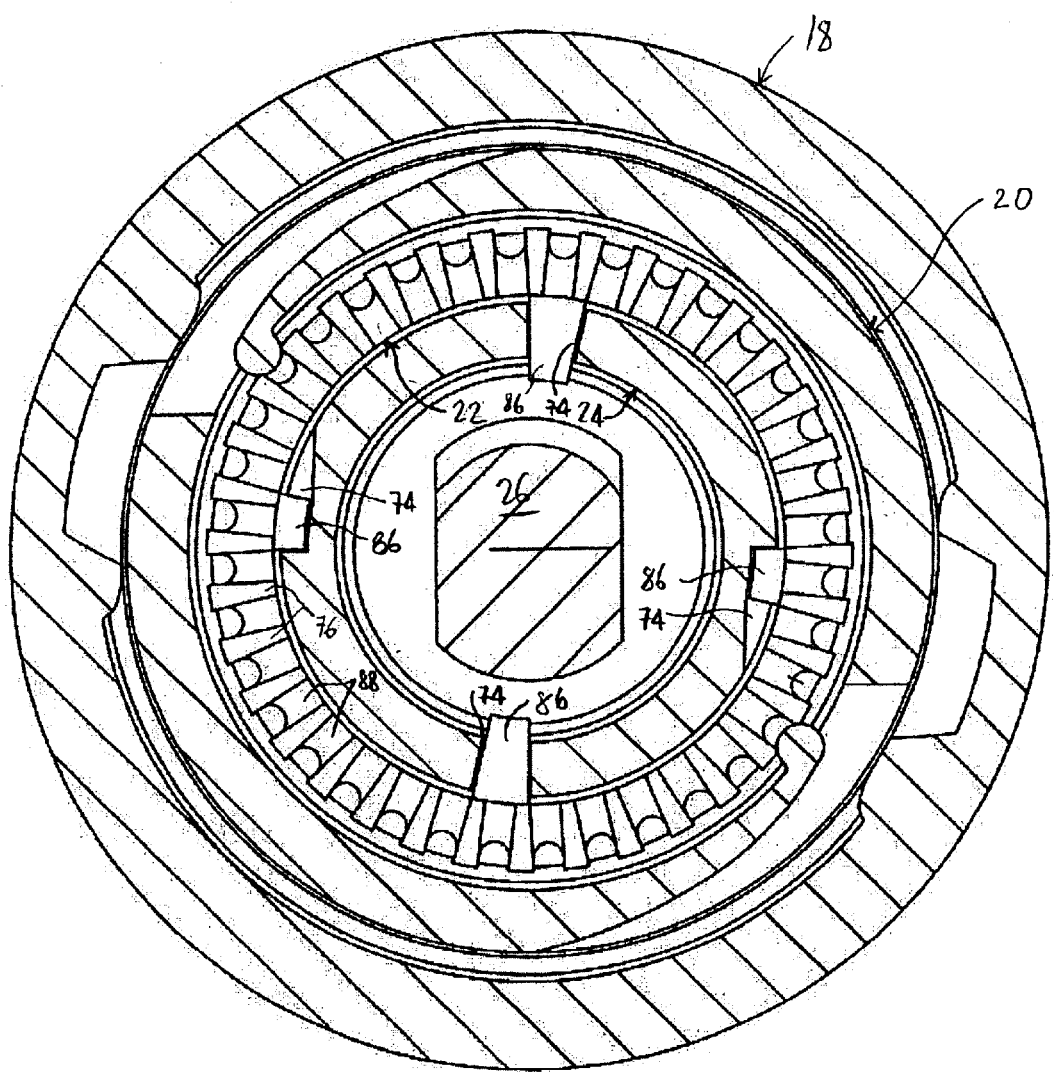
FIG. 9 is a cross-sectional view taken along line 9—9 of FIG. 7.

Dosing ring 22 is formed with one or more grooves 76 at a proximal end 78 thereof; a plurality of longitudinal ribs 80; a snap ring 82 in proximity to a distal end 84 thereof; and, inwardly extending splines 86 formed and located to be disposed in the keyways 74 of the driver 24. As best shown in FIG. 9, in assembling the pen 10, the dosing ring 22 is mounted onto the driver 24 with the splines 86 extending into the keyways 74. As a result, the dosing ring 22 cannot be rotated relative to the driver 24. However, the splines 86 are formed such to allow the dosing ring 22 to axially move along the length of the keyways 74. Also, as shown in FIG. 9, the grooves 76 are preferably formed on the proximal end 78 to face axially and are formed about the entire periphery thereof, more preferably, at equal intervals. The grooves 76 are separated by partitions 88, which may be rounded to facilitate engagement of the grooves 76 with the teeth of the dose knob 20 described below.

The dose knob 20 is generally tubular having open proximal and distal ends 90 and 92, respectively. A textured handle 94 is formed in proximity to the distal end 92 which is engageable by a user to rotate the dose knob 20 in setting the pen 10 to a desired dosage amount. The dose knob 20 includes one or more thread portions 95 (FIG. 11) formed to threadedly engage the dose setting thread 54 of the body 18. Accordingly, the dose knob 20 may be rotated within the body 18 resulting in translation of that rotation to axial displacement of the dose knob 20 relative to the body 18 in setting a desired dosage. Dosage indicia (not shown) may also be disposed externally of the dose knob 20.

Figure 8:
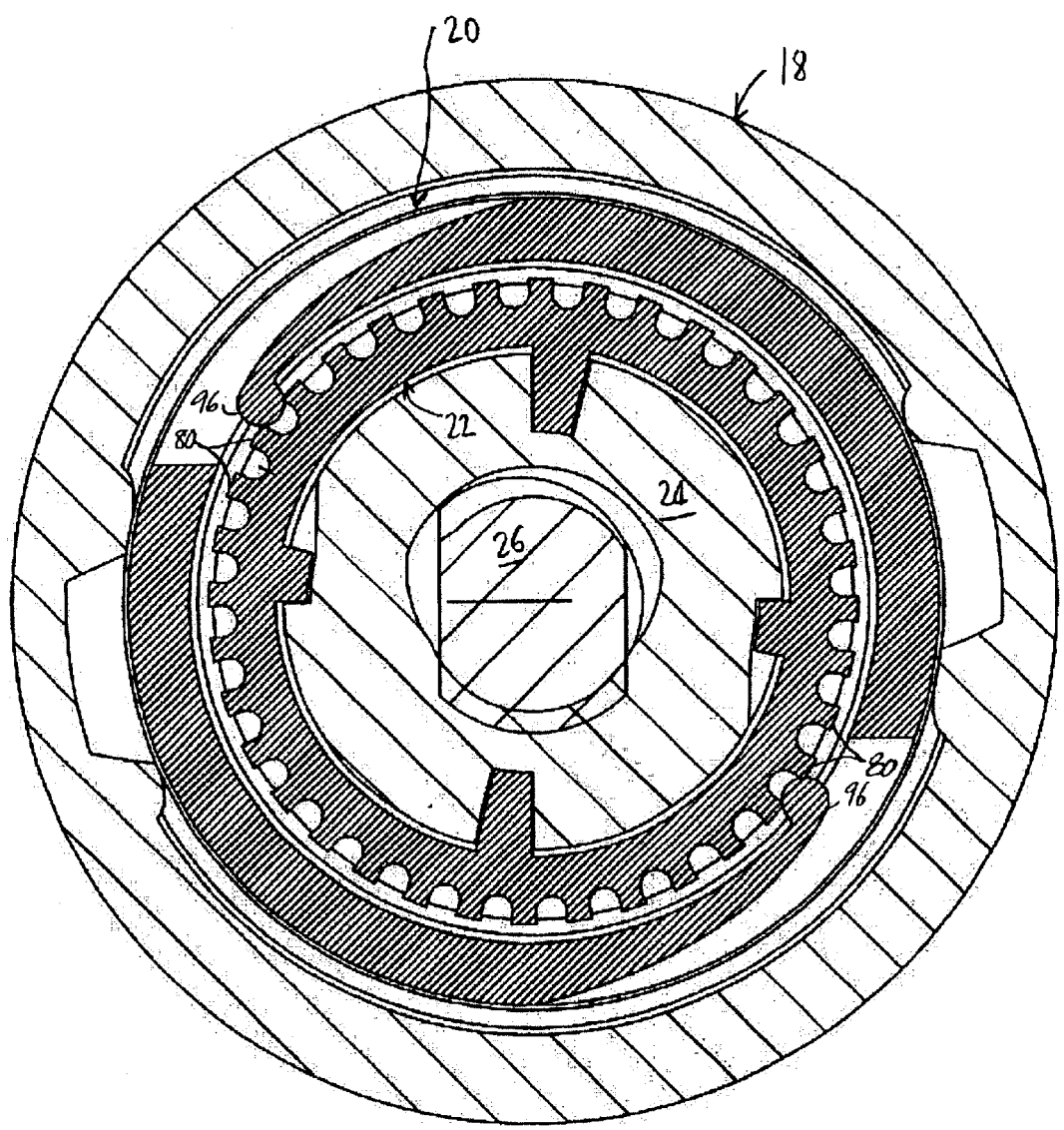
FIG. 8 is a cross-sectional view taken along line 8—8 of FIG. 7.

The dose knob 20 preferably includes one or more ratchet arms 96 formed to be biased inwardly. With reference to FIG. 8, with the dose knob 20 being coaxially disposed about the dosing ring 22, the ratchet arms 96 are aligned with the longitudinal ribs 80 so that rotation of the dose knob 20 relative to the dosing ring 22 results in the ratchet arms 96 acting against the ribs 80 in a ratcheting manner giving a user an audible signal of such rotation. In contrast to the prior art, the dose knob 20 can freely rotate in both directions relative to the dosing ring 22 with the ratchet arms 96 acting against the ribs 80 during both rotational directions of the dose knob 20.

Figure 10:
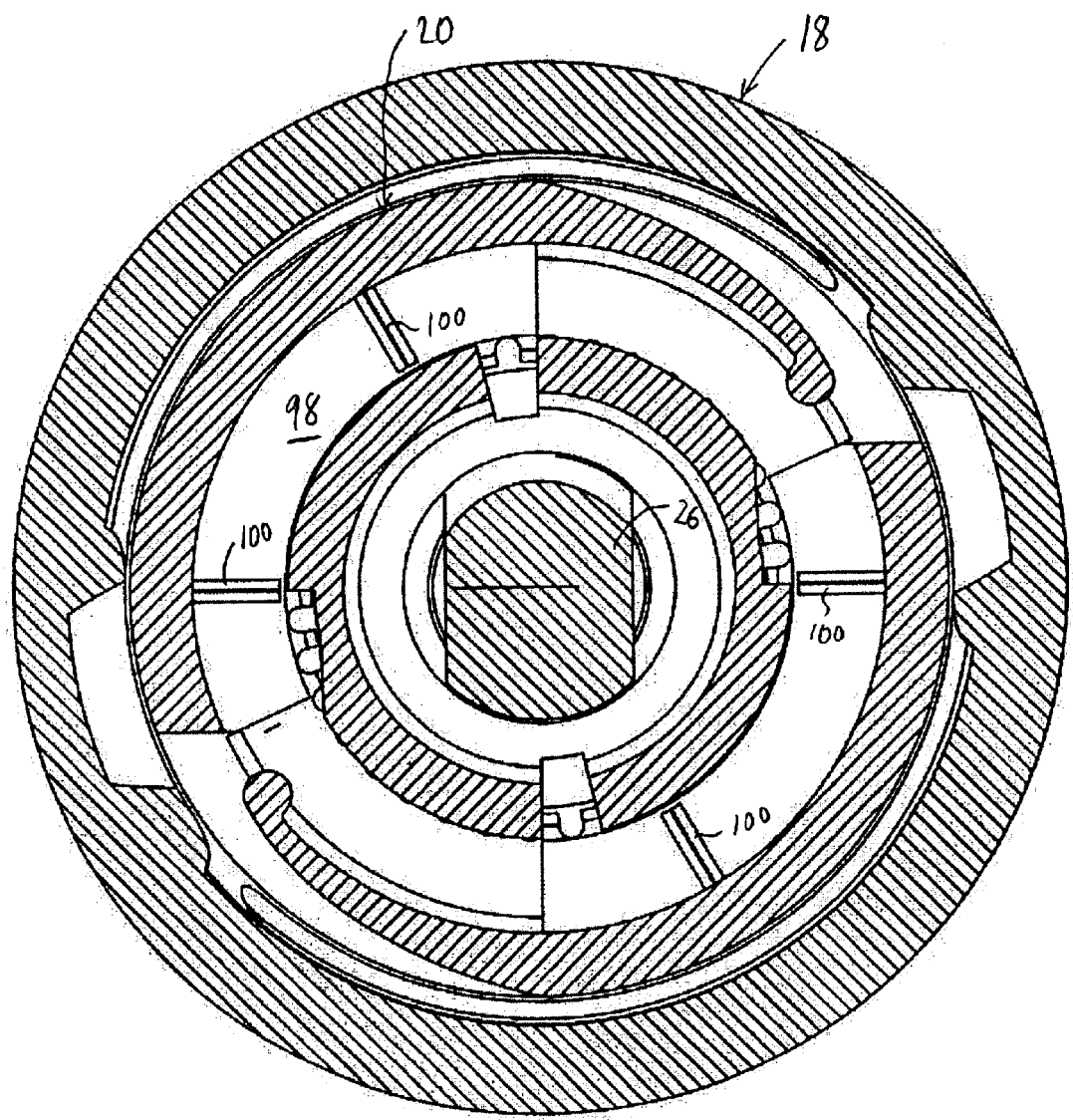
FIG. 10 is a cross-sectional view taken along line 10—10 of FIG. 7.

The dose knob 20 is also formed with one or more lips 98 (FIG. 2) which are formed in proximity to the proximal end 90 and from which extend one or more teeth 100. The teeth 100 are formed and positioned to be received in the grooves 76 formed on the dose knob 20 and preferably face axially with regard to the longitudinal axis of the dose knob 20. With reference to FIG. 10, the teeth 100 are much less in number than the grooves 76 to facilitate alignment.

The dosing ring 22 is mounted onto the dosing ring adaptor 28 with the snap ring 82 of the dosing ring 22 snapping into locking channel 102 defined in the dosing ring adaptor 28. As such, the dosing ring 22 and the dosing ring adaptor 28 are movable in concert with each other. In an alternative embodiment, the dosing ring adaptor 28 and the dosing ring 22 may be formed unitarily.

The leadscrew 26 may be of any conventional type and is formed with a threaded end 103. The spinner 16 includes a threaded aperture 105 formed to threadedly engage the threaded end 103 in mounting the spinner 16 onto the leadscrew 26. Alternatively, the thumb button 30 is of any conventional design and formed to snap onto the dose ring adaptor 28. The thumb button 30 may be unitarily formed with the dose ring adaptor 28.

Figure 11:
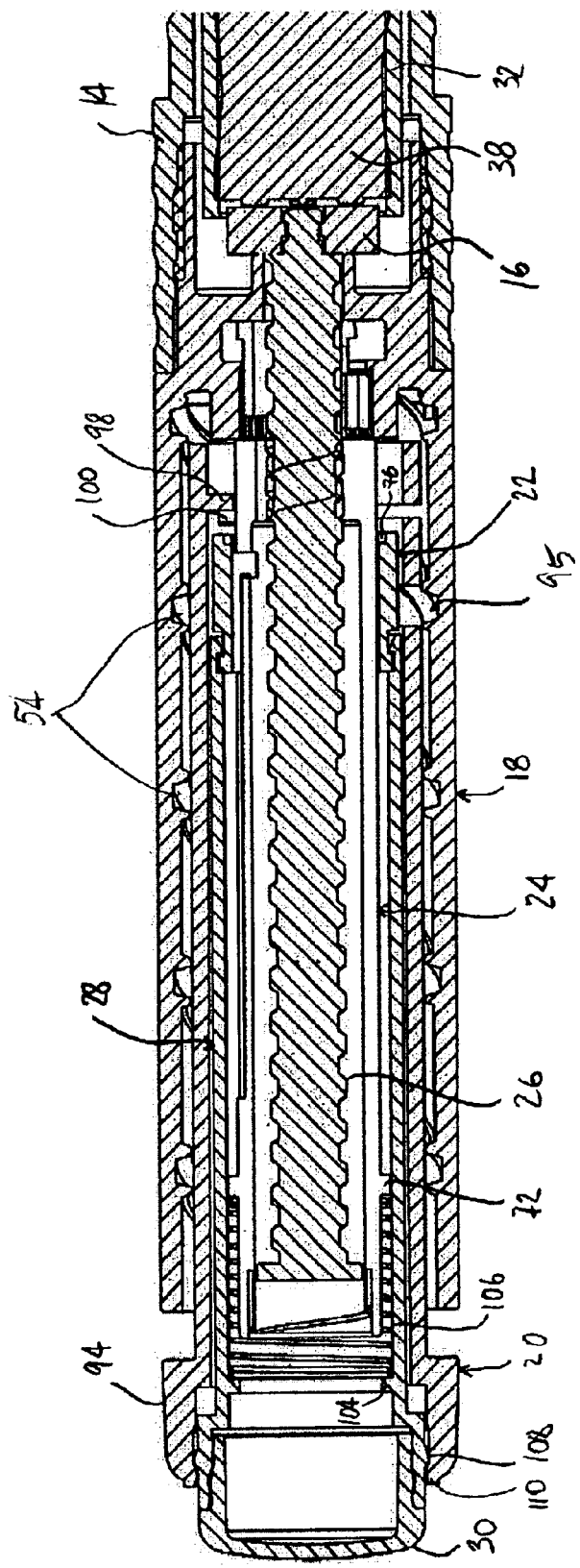
FIGS. 11 and 12 are partial cross-sectional views showing, respectively, the medication delivery pen in a rest state and in an initial dosing state.
Figure 12:
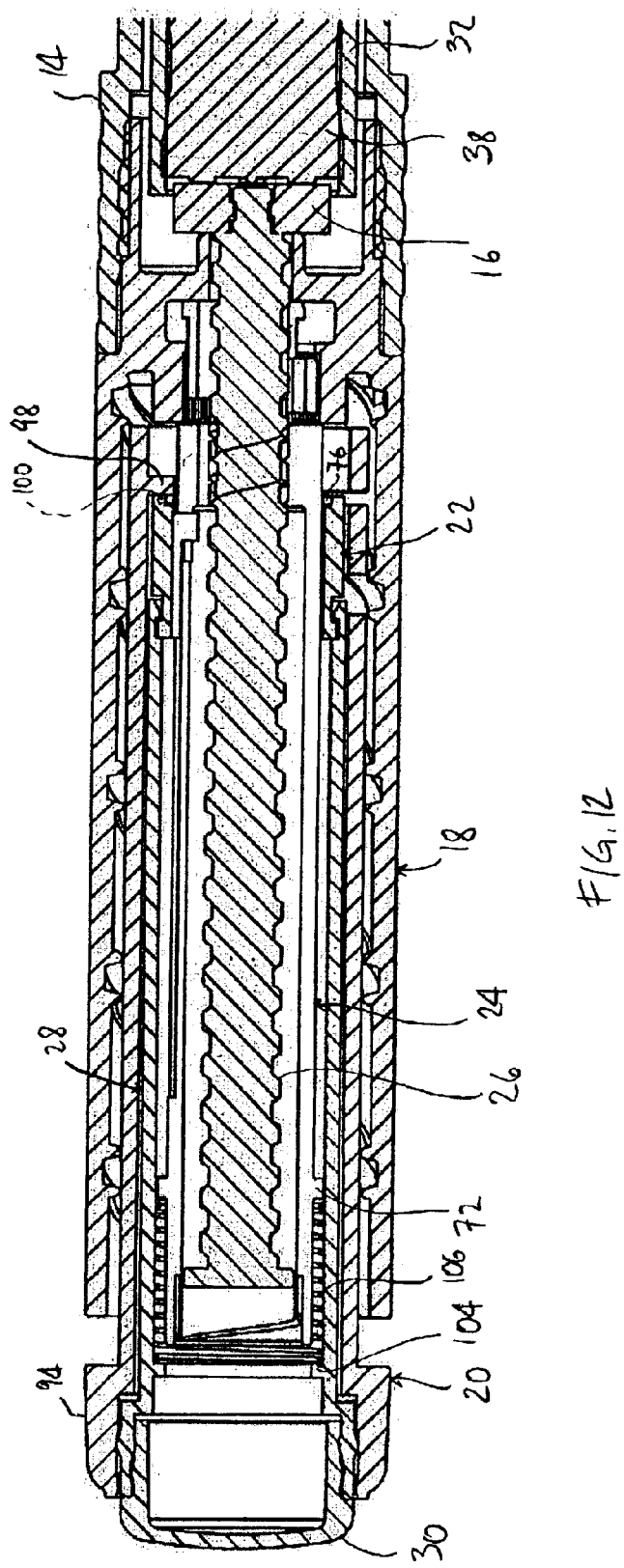

With reference to FIGS. 7, 11 and 12, the dosing ring adaptor 28 includes an inwardly extending shoulder 104. With the pen 10 being fully assembled, a biasing means 106, such as a coil spring, is preferably disposed between the ledge 72 of the driver 24 and the shoulder 104 of the dosing ring adaptor 28. Consequently, the dosing ring adaptor 28 is urged distally within the pen 10, along with the dosing ring 22. Stop member 108 may be provided on the dosing ring adaptor 28 formed to abut against inwardly-extending ring 110 defined on the dose knob 20 under force of the biasing means 106 to limit distal movement of the dosing ring adaptor 28.

Referring to FIG. 11, in a rest state, the dosing ring 22 is urged into a rest position with the grooves 76 being spaced from the teeth 100 of the dose knob 20. Accordingly, the dose knob 20 can be freely rotated without rotating the dosing ring 22. In this manner, the dose knob 20 can be rotated within the body 18 (with rotational movement being translated into axial displacement) and set to a desired dosage in a manner similar to prior art devices. With the dose knob 20 thus translating, the dosing ring adaptor 28, the biasing means 106 and the dosing ring 22 move therewith, while the dosing ring 22 remains in its rest position. The dosing ring 22 slides axially long the driver 24 as a proper dose is selected. The subject invention, unlike the prior art, allows the dose knob 20 to be "dialed back" freely if a desired dosage amount is inadvertently by-passed, without the undesirable and costly effect of expelling medication.

In a preferred embodiment, with a desired dosage amount being set, the ratchet arms 96 advantageously provide holding force to maintain the desired radial position of the dose knob 20 relative to the dosing ring 22, and, thus, to the driver 24. In other words, the dose knob 20 cannot rotate without overcoming this holding force.

The needle cannula may be attached to the pen 10 prior to or after setting the desired dosage, as a matter of user preference. Once the needle cannula has been prepared, attached to the cartridge holder 14, and inserted into the patient, the thumb button 30 is depressed. Initially, the applied force will act against the biasing means 106 causing initial straight-line motion of the dosing ring adaptor 28 and eventual interengagement of the grooves 76 and the teeth 100, as shown in FIG. 12. Additional force will cause the dose knob 20 to rotate in descending along the dose setting thread 54 in a proximal direction. With the interengagement of the grooves 76 and the teeth 100, the dosing ring 22 rotates with the dose knob 20. In turn, the driver 24 rotates with the dosing ring 22 (due to the interengagement of the keyways 74 and the splines 86), and the threads 68 of the driver 24 rotate about the threads 70 of the leadscrew 26. Since the leadscrew 26 cannot rotate because of its fixed positioning in the aperture 46, the leadscrew 26 axially translates in a proximal direction to urge the spinner 16 against the plunger 38 in expelling medication from the drug cartridge 32. The volume of the drug to be expelled is calibrated to the settings of the dose knob 20.

Once a dose has been administered, the thumb button 30 is released, causing the dosing ring 22 to return to its rest position. The dose knob 20 can then be adjusted to a zero position ready for the next drug administration. The spinner 16 does not move in setting a dosage amount and, thus, is at a zero position after each dose administration. In the preferred embodiment, to maintain the spinner 16 position accurately, the interengagement of the ratchet teeth 52 and the ratchet fingers 66 prevents undesired rearward rotation of the driver 24 that would result in the leadscrew 26 possibly translating distally. The administration process is repeated until the drug cartridge 32 is spent. If the pen 10 is reusable, the cartridge can be replaced, whereas, if the pen is disposable, the entire pen 10 may be disposed of.

As will be appreciated by those skilled in the art, various modifications can be made with the spirit of the invention being maintained. For example, grooves may be formed on the dose knob and teeth on the dosing ring, or a combination thereof.

While the invention has been described in relation to the preferred embodiments with several examples, it will be understood by those skilled in the art that various changes may be made without deviating from the spirit and scope of the invention as defined in the appended claims.

What is claimed is:

1. A medication delivery pen for expelling medication from a medicine cartridge, said pen comprising:
   a driver;
   a dosing ring non-rotatably disposed on said driver and axially slidable thereon and therealong; and,
   a dose knob coaxially disposed about said dosing ring, wherein at least one tooth is formed on one of said dose knob and said dosing ring, and wherein at least one groove is formed on the other of said dose knob and said dosing ring, said tooth and said groove being formed for selective cooperative engagement with each other;
   wherein said dosing ring is selectively movable axially relative to said dose knob from a first position where said tooth and said groove are spaced apart from each other, to a second position where said tooth and said groove are cooperatively engaged with each other such that said dosing ring is rotatable with said dose knob when said dosing ring is in said second position.

2. A pen as in claim 1, further comprising biasing means to urge said dosing ring into said first position.

3. A pen as in claim 2, wherein said biasing means is a coil spring.

4. A pen as in claim 1, wherein said second position is a medication delivery position in which said pen is used to deliver medication.

5. A pen as in claim 1, wherein said dosing ring having a plurality of longitudinal ribs, said dose knob having at least one inwardly biased ratchet arm to resiliently act against said ribs upon relative motion between said dosing ring and said dose knob.

6. A pen as in claim 1, further comprising a body coaxially disposed about said dose knob, said dose knob threadedly engaging said body.

7. A pen as in claim 1, further comprising a leadscrew having a plurality of threads, where said driver is coaxially disposed about a portion of said leadscrew and includes internal threads for threadedly engaging said leadscrew.

8. A pen as in claim 7, further comprising a body coaxially disposed about said dose knob, said body including an aperture through which said leadscrew passes, said aperture being formed to prevent rotation of said leadscrew relative to said body.

9. A pen as in claim 1, further comprising a body coaxially disposed about said dose knob, said dose knob having an externally defined thread portion, said body having an internally defined thread for receiving said thread portion, said thread portion and said thread translating rotational movement into axial displacement when said dose knob is selectively rotated by a user.

10. A pen as in claim 9, further comprising a cartridge holder within which the medicine cartridge may be provided.

11. A pen as in claim 10, wherein said cartridge holder is removably secured to said body.

12. A pen as in claim 10, wherein said cartridge holder is fixedly secured to said body.

13. A medication delivery pen for expelling medication from a medicine cartridge, the medicine cartridge having a pierceable septum sealing one end, a needle cannula being removably securable to the one end for piercing the septum, said pen comprising:
   a leadscrew having a plurality of threads;
   a driver coaxially disposed about a portion of said leadscrew;
   a dosing ring non-rotatably disposed on said driver and axially slidable thereon and therealong;
   a dose knob coaxially disposed about said dosing ring and selectively rotatable by a user, wherein said dose knob has a first feature defined thereon and said dosing ring has a second feature defined thereon, said first and said second features being complementary with each other and being selectively operatively engageable with each other;
   said dosing ring being biased into a first position wherein said first feature and said second feature are not operatively engaged with each other, said dosing ring being selectively movable from said first position to a second position in which said first feature and said second feature are operatively engaged with each other to lockingly engage said dose knob and said dosing ring so as to allow medicine to be expelled from the cartridge through the needle cannula.

14. A pen as in claim 13, further comprising a coil spring for biasing said dosing ring into said first position.

15. A pen as in claim 13, further comprising a body coaxially disposed about said dose knob, said dose knob having an externally defined thread portion, said body having an internally defined thread for receiving said thread portion, said thread portion and said thread translating rotational movement into axial displacement when said dose knob is selectively rotated by a user.

16. A pen as in claim 15, further comprising a cartridge holder within which the medicine cartridge may be provided.

17. A pen as in claim 16, wherein said cartridge holder is removably secured to said body.

18. A pen as in claim 16, wherein said cartridge holder is fixedly secured to said body.

* * * * *